United States Patent [19]

Sen-Jung

[11] Patent Number: 4,578,082
[45] Date of Patent: Mar. 25, 1986

[54] FLUID CUSHIONING APPARATUS ACTING AS A PIVOTING MEDIUM OF TWO OBJECTS HAVING A PIVOTING FEATURE

[76] Inventor: Chen Sen-Jung, No. 236, Sec. 3, Ho Ping W. Rd., Taipei, Taiwan

[21] Appl. No.: 567,798

[22] Filed: Jan. 3, 1984

[51] Int. Cl.⁴ .......................... A61F 2/72; A61F 2/74; A61F 2/62; F16M 1/00
[52] U.S. Cl. ........................................ 623/26; 623/27; 623/39; 267/113; 267/124; 267/140.1
[58] Field of Search ................... 267/11 A, 113, 118, 267/124, 140.1; 3/1.2, 2, 22-29

[56] References Cited

U.S. PATENT DOCUMENTS

| 2,421,585 | 6/1947 | Thiry | 267/140.1 |
| 2,519,226 | 8/1950 | Coe, Jr. | 3/1.2 UX |
| 2,533,008 | 12/1950 | Hanson | 3/1.2 |
| 2,830,301 | 4/1958 | Schober | 3/1.2 UX |
| 3,642,268 | 2/1972 | Hipsher | 267/140.1 X |
| 4,065,815 | 1/1978 | Sen-Jung | 3/1.2 |
| 4,212,087 | 7/1980 | Mortensen | 3/1.2 |

FOREIGN PATENT DOCUMENTS

| 2457042 | 7/1975 | Fed. Rep. of Germany | 267/113 |
| 886569 | 1/1962 | United Kingdom | 3/26 |

Primary Examiner—Ronald L. Frinks
Attorney, Agent, or Firm—Knobbe, Martens, Olson & Bear

[57] ABSTRACT

A fluid cushioning apparatus acting as a pivoting medium of two objects having a pivoting feature includes a sleeve, a shaft and a partitioning piece. The shaft has two radially enlarged annulations being closely and rotatably mounted in the sleeve and a dividing wall being axially and radially extended between the two annulations to closely engage with the interior wall of the sleeve. The sleeve is mounted on a first object and the shaft is mounted on a second object which is always to have a pivoting relationship with the first object. The partitioning piece is capable of being closely fitted among the sleeve, the shaft and the two annulations and is secured on the sleeve so that the space formed between the shaft and the sleeve is divided into two compartments. The shaft is a hollow member one end of which is mounted a replenishing cushioning fluid supplier while the other end of which is mounted a check valve and a first hole is provided on the shaft so that the liquid supplier will supply the space with new cushioning fluid through the check valve and the first hole when there is a fluid loss in the space. The shaft is further provided with a second hole to let the fluid contained in one of the two compartments flow through the first and second holes to the other one compartment when the first and second object are in relative pivoting movement to obtain a neat cushioning effect.

7 Claims, 6 Drawing Figures

FLUID CUSHIONING APPARATUS ACTING AS A PIVOTING MEDIUM OF TWO OBJECTS HAVING A PIVOTING FEATURE

BACKGROUND OF THE INVENTION

The present invention relates to a fluid cushioning apparatus, and more particularly to a fluid cushioning apparatus which itself acts as a pivoting medium of two objects having a pivoting feature.

A typical prior fluid cushioning apparatus, as shown in FIG. 1, includes a hydraulic cylinder 1, a separating piece 2 fixed to cylinder 1, a piston rod 3 and two pistons 4, 5 secured on rod 3. Piece 2 is penetrated by rod 3 and kept a liquid tight relation with rod 3. Thus, cylinder 1 is formed into two compartments 6, 7. When rod 3 is actuated by connecting rod 8 to move up or down the liquid contained in the compressed compartment will flow through a passage 9 to the other compartment. The liquid flow through passage 9 is controlled by a needle valve 10 and thus a cushioning effect is achieved, i.e. rod 3 will move slowly because piston 4 or 5 is cushioned by the compressed liquid contained in the compressed compartment. Such a cushioning device is widely used in a field which has two objects in pivoting relation and needs a cushioning result. An example of incorporating such a device is shown in FIG. 2 which shows an artificial leg 11 having a thigh part 12 and a shank part 13 pivoted together on a knee part 14. The device is incorporated within shank part 13 and connecting rod 8 is pivoted on knee part 14 so that connecting rod 8 actuates piston rod 3 up and down when thigh part 12 is lifted down and up to obtain a cushioned movement for the amputee who wears artificial leg 11. A returning spring 15 is compressed when rod 3 is urged downwardly and thus is helpful to assist the amputee to stand up. However, such a device suffers the following disadvantages. The first, such a device takes so much a volume and a weight. The second, such a device has a hydraulic liquid loss due to frequent reciprocating movements, and thus cylinder 1 is not always full of hydraulic liquid and the cushioned movement is not smooth and happens to be in vibration, and the hydraulic liquid has to be refilled from time to time. It is therefore tried by the applicant to obviate the above disadvantages.

SUMMARY OF THE INVENTION

According to the present invention, a fluid cushioning apparatus acting as a pivoting medium of two objects having a pivoting feature includes a sleeve adapted to be mounted on a first object, two annulations coaxially mounted in the two ends of the sleeve respectively, a shaft mounted in the openings of the centers of the two annulations and having a dividing wall being axially and radially extended between the two annulations to closely engage with the interior wall of the sleeve and being adapted to be mounted on a second object which is always to have a pivoting relationship with the first object, a partitioning piece capable of being fitted among the sleeve, the shaft and the two annulations and secured on the sleeve so that the space formed among the shaft, the two annulations and the sleeve is divided into two compartments and a means controlling the flow of a fluid contained in the space when the first and second objects are in relative pivoting movement and thus the fluid contained in one of the two compartments will flow through the means to the other one compartment so that the pivoting movement of the first and second objects is cushioned by the controlled fluid flow.

The two annulations can be integrally formed with the sleeve.

Certainly, the two annulations can also be integrally formed to the shaft and be closely and rotatably mounted in the sleeve.

The partitioning piece can also be integrally formed to the sleeve and the annulations be detachably mounted on the shaft.

Preferably the shaft is a hollow member one end of which is mounted a replenishing cushioning fluid supplier while the other end of which is mounted a check valve and the shaft has a first hole so that the fluid supplier will supply the space with new cushioning fluid through the check valve and the first hole when there is a fluid loss in the space.

The controlling means can be an orifice of an appreciable small size on the partitioning piece to allow a little rate of the fluid flow.

Generally, the partitioning piece is closely fitted among the sleeve, the shaft and the two annulations and the controlling means is a second hole on the shaft so that the fluid contained in one of the two compartments will flow through the first and second holes to the other one compartment when the first and second objects are in relative pivoting movement.

The check valve can include a ball, a ball seat formed on the interior wall of the shaft for receiving the ball, a spring engaging with the ball from a direction opposite to that of the ball seat engaging with the ball and a first plug having a first threaded head screwed into the other end to urge the spring against the ball and capable of shielding the second hole so that both of the opening of the second hole and the pre-determined spring pressure on the ball can be adjusted by screwing the first plug.

The replenishing cushioning fluid supplier can include a second plug having a second threaded head screwed into the one end, a spring having a first end engaged with the second plug and second end and a piston engaged with the second end and capable of slidably and closely engaging with the interior wall of the shaft so that the fluid contained between the piston and the ball seat is ready for replenishing the space with new fluid through the check valve.

The first object can be the shank of an artificial leg and the second object can be the thigh of the artificial leg.

The cushioning fluid used can be a hydraulic liquid or a gas.

It is therefore an object of the present invention to provide a fluid cushioning apparatus acting as a pivoting medium of two objects having a pivoting feature having a small volume and weight.

It is therefore another object of the present invention to provide a fluid cushioning apparatus acting as a pivoting medium of two objects having a pivoting feature having a cylinder which is always full of fluid to secure a smooth cushioned movement.

These and other advantages of the present invention may best be understood with reference to the accompanying drawings, in which

DETAILED DESCRIPTION OF THE PREFERRED EMBODIMENT

Figure 1:
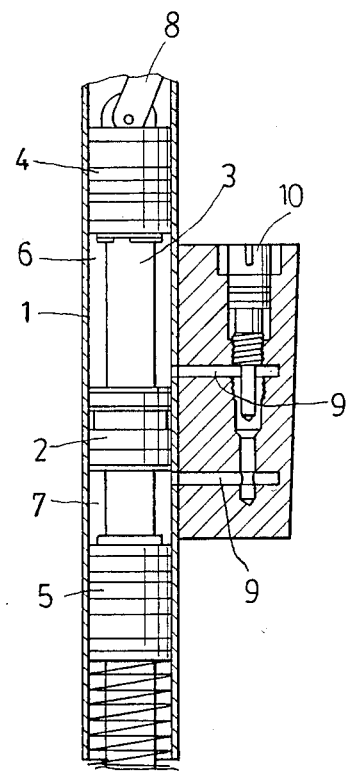
FIG. 1 is a sectional view showing a hydraulic cylinder of the known hydraulic cushioning apparatus.
Figure 2:
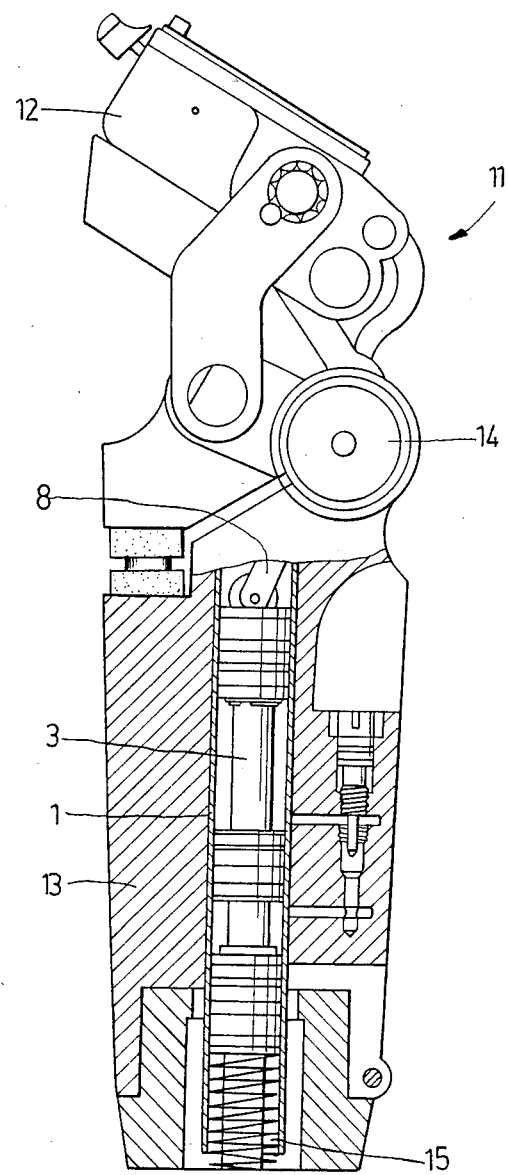
FIG. 2 is a sectional view showing an artificial leg incorporating a known hydraulic cushioning apparatus.
Figure 3:
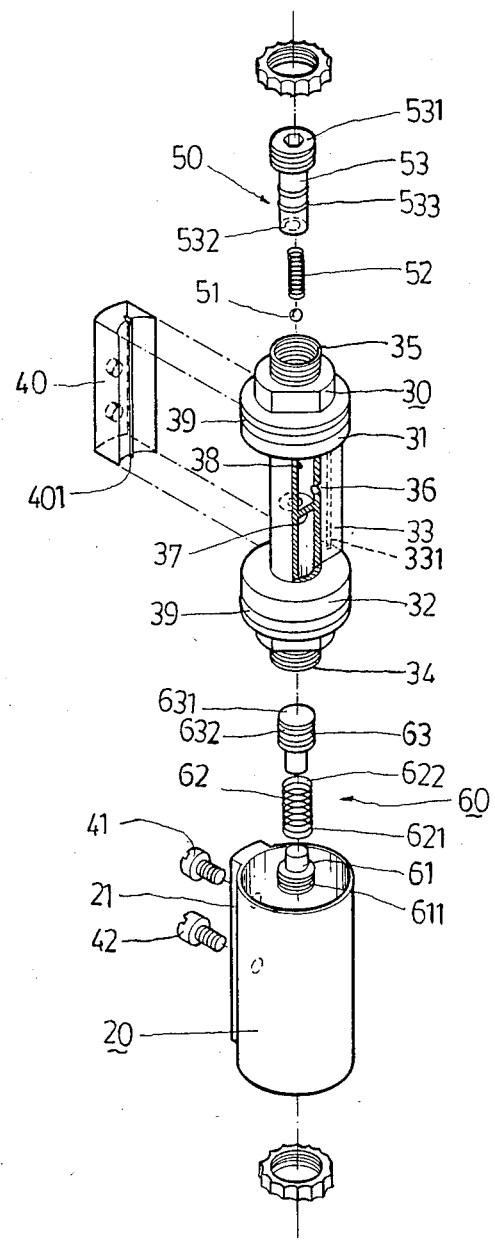
FIG. 3 is an exploded view showing the elements of a preferred embodiment of a fluid cushioning apparatus acting as a pivoting medium of two objects having a pivoting feature of the present invention.

Referring now to FIG. 3, there is shown an exploded view of a fluid cushioning apparatus of the present invention which includes a sleeve 20, a shaft 30 and a partitioning piece 40. Shaft 30 has two radially enlarged annulations 31, 32 and a dividing wall 33 being radially and axially extended between annulations 31, 32. Annulations 31, 32 and dividing wall 33 can be closely rotated within sleeve 20. A partitioning piece 40 capable of closely fitted among sleeve 20, shaft 30 and annulations 31, 32 is secured on a thickened place 21 on sleeve 20 by two screws 41, 42 so that the space defined by shaft 30 and sleeve 20 is divided into two compartments 70, 80 by partitioning piece 40 and dividing wall 33, as shown in FIG. 4B which shows a transverse section view of a cushioning apparatus of the present invention. Shaft 30 is a hollow member one end of which 34 is mounted a replenishing cushioning fluid supplier 60 while the other end of which 35 is mounted a check valve 50 and shaft 30 has a first hole 36 so that liquid supplier 60 will supply the space with new cushioning fluid through check valve 50 and hole 36 when there is a fluid loss in the space.

Check valve 50 includes a ball 51, a ball seat 37 formed on the interior wall of shaft 30 for receiving ball 51, a spring 52 and a first plug 53 having a first threaded head 531 screwed into end 35 to urge spring 52, ball 51 against ball seat 37.

Replenishing cushioning fluid supplier 60 includes a second plug 61 having a second threaded head 611 screwed into end 34, a spring 62 having a first end 621 engaged with second plug 61 and a piston 63 engaged with a second end 622 of spring 62. Piston 63 is capable of slidably and closely engaging with the interior wall of shaft 30 so that the cushioning fluid contained between piston 63 and ball seat 37 is ready for replenishing the space with new fluid should there is any fluid loss in compartments 70, 80 by way of spring 62 upwardly urging the top end 631 of piston 63 to push the fluid contained between top end 631 and ball seat 37 to pass through check valve 50.

A second hole 38 on shaft 30 and first hole 36 permit the communication of the cushioning fluid between compartments 70, 80. Thus, when sleeve 20 and shaft 30 are in relative pivoting movement partitioning piece 40 forces the liquid contained in compartment 70 (80) to pass slowly through holes 36, 38 to the other compartment 80 (70). It is therefore that the pivoting movement is cushioned by the compressed fluid. An end 532 of plug 53 is designed to shield hole 38 when head 531 is further screwed into end 35 and plug 53 can adjust the pre-determined pressure of spring 52 on ball 51 by screwing plug 53 up or down.

Figure 4A:
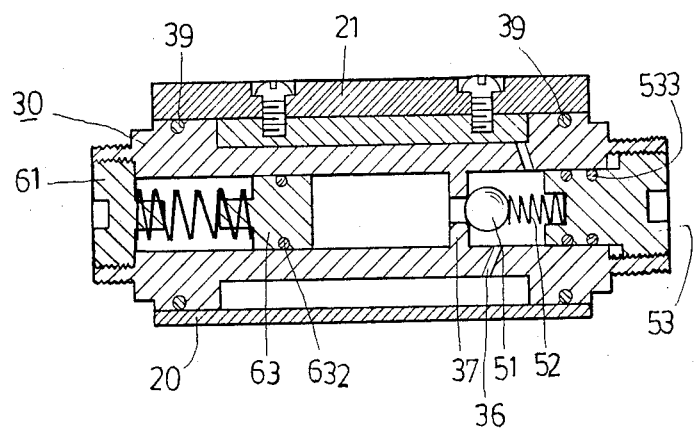
FIG. 4A is a longitudinal section view of a preferred embodiment of the present invention.
Figure 4B:
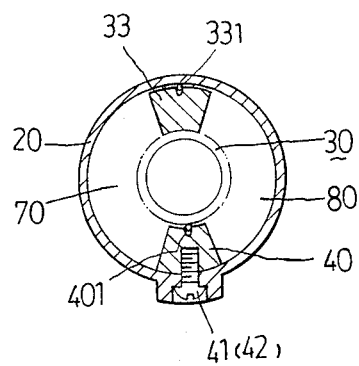
FIG. 4B is a transverse section view of a preferred embodiment of the present invention.

FIG. 4A shows a longitudinal section view of a cushioning apparatus of the present invention. The rotating parts are fitted with gasket rings 39 on shaft 30, 533 on plug 53 and 632 on piston 63 or gasket strips 331 on dividing wall 33 and 401 on partitioning piece 40.

Figure 5:
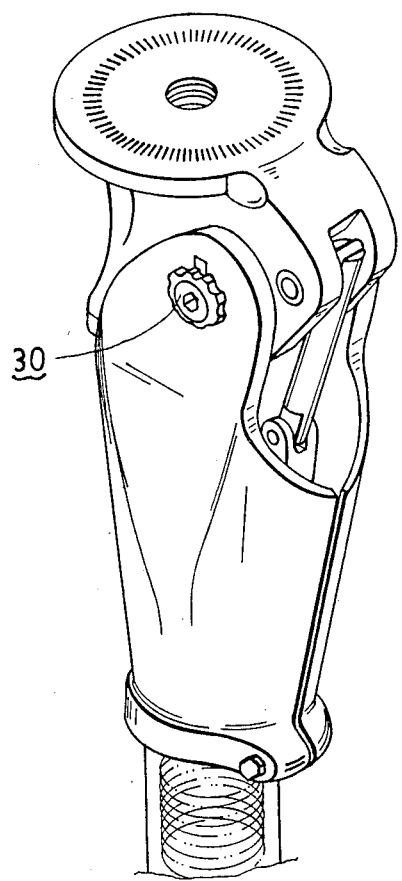
FIG. 5 is a perspective view showing the knee part of an artificial leg incorporating a hydraulic cushioning apparatus acting as a pivoting medium of two objects having a pivoting feature of the present invention.

FIG. 5 shows a fluid cushioning apparatus acting as a pivoting medium of two objects having a pivoting feature of the present invention incorporated into the knee part of an artificial leg. The thickened place 21 on sleeve 20 can directly be locked in a groove formed on the knee part so that no additional procedure is needed to secure sleeve 20 on the knee part.

While the present invention has been described in connection with what is presently considered to be the most practical and preferred embodiment, it is to be understood that the invention is not to be limited to the disclosed embodiments but on the contrary, is intended to cover various modifications and equivalent arrangements included within the spirit and scope of the appended claims which scope is to be accorded the broadest interpretation so as to encompass all such modifications and equivalent structures.

What I claim is:

1. A fluid cushioning apparatus acting as a pivoting medium of two objects having a pivoting feature comprising:

a sleeve adapted to be mounted on a first object; two annulations coaxially mounted in the two ends of said sleeve respectively;

a shaft mounted in the openings of the centers of said two annulations and having a dividing wall being axially and radially extended between said two annulations to closely engage with the interior wall of said sleeve and being adapted to be mounted on a second object which is always to have a pivoting relationship with said first object;

a partitioning piece capable of being fitted among said sleeve, said shaft and said two annulations and secured on said sleeve so that the space formed between said shaft and said sleeve is divided into two compartments; and a means controlling the flow of a cushioning fluid contained in said space when said first and second objects are in relative pivoting movement and thus the fluid contained in one of said two compartments will flow through said means to the other one compartment so that said pivoting movement of said first and second objects is cushioned by said controlled fluid flow.

2. A fluid cushioning apparatus acting as a pivoting medium of two objects having a pivoting feature according to claim 1 wherein said two annulations are integrally formed to said shaft and are closely and rotatably mounted in said sleeve.

3. A fluid cushioning apparatus acting as a pivoting medium of two object having a pivoting feature according to claim 2 wherein said shaft is a hollow member one end of which is mounted a replenishing cushioning fluid supplier while the other end of which is mounted a check valve and said shaft has a first hole so that said fluid supplier will supply said space with new cushioning fluid through said check valve and said first hole when there is a liquid loss in said space.

4. A fluid cushioning apparatus acting as a pivoting medium of two objects having a pivoting feature according to claim 3 wherein said partitioning piece is closely fitted among said sleeve, said shaft and said two annulations and said controlling means is a second hole on said shaft so that said fluid contained in one of said two compartments will flow through said first and second holes to the other one compartment when said first and second objects are in relative pivoting movement.

5. A fluid cushioning apparatus acting as a pivoting medium of two objects having a pivoting feature according to claim 4 wherein said check valve comprises:
   a ball;
   a ball seat formed on an interior wall of said shaft for receiving said ball;
   a spring engaging with said ball from a direction opposite to that of said ball seat engaging with said ball; and
   a first plug having a first threaded head screwed into said the other end to urge said spring against said ball and being capable of shielding said second hole so that both of the opening of said second hole and the pre-determined spring pressure on said ball can be adjusted by screwing said first plug.

6. A fluid cushioning apparatus acting as a pivoting medium of two objects having a pivoting feature according to claim 5 wherein said replenishing cushioning fluid supplier comprising:
   a second plug having a second threaded head screwed into said one end;
   a spring having a first end engaged with said second plug and a second end; and
   a piston engaged with said second end and capable of slidably and closely engaging with said interior wall of said shaft so that the cushioning fluid contained between said piston and said ball seat is ready for replenishing said space with new fluid through said check valve.

7. A fluid cushioning apparatus acting as a pivoting medium of two objects having a pivoting feature according to claim 6 wherein said first object is the knee of an artificial leg and said second object is the thigh of said artificial leg.

* * * * *